(12) United States Patent
Hsiue et al.

(10) Patent No.: US 6,503,998 B2
(45) Date of Patent: Jan. 7, 2003

(54) LAMBDA-SHAPED CARBAZOLE AND MAIN-CHAIN NLO POLYURETHANE CONTAINING THE SAME

(75) Inventors: Ging-Ho Hsiue, Hsinchu (TW); Wen-Jang Kuo, Yunlin Hsien (TW); Ru-Jong Jeng, Taichung (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/946,582

(22) Filed: Sep. 5, 2001

(65) Prior Publication Data

US 2002/0115869 A1 Aug. 22, 2002

(30) Foreign Application Priority Data

Dec. 14, 2000 (TW) .......................................... 089126718

(51) Int. Cl.[7] .............................................. C08G 18/64
(52) U.S. Cl. ........................ 528/74; 548/427; 548/439; 548/440
(58) Field of Search ................................ 548/427, 439, 548/440; 528/74

(56) References Cited

U.S. PATENT DOCUMENTS 5,736,284 A * 4/1998 Kobayashi et al.

* cited by examiner

Primary Examiner—Rachel Gorr
(74) Attorney, Agent, or Firm—Fish & Richardson P.C.

(57) ABSTRACT

The present invention provides a lambda-shaped carbazole based chromophore, and a main-chain NLO polyurethane containing the same. The lambda-shaped structure reduces the plasticization to the main-chain polymers caused by the chromophore and increases temporal stability of the NLO coefficients of the main-chain NLO polyurethane. The NLO coefficients of the main-chain NLO polyurethane are stable because the efficiency of dipole alignment in electric field is increased due to the dipole thereof being perpendicular to the main chain of the polyurethane.

7 Claims, 4 Drawing Sheets

LAMBDA-SHAPED CARBAZOLE AND MAIN-CHAIN NLO POLYURETHANE CONTAINING THE SAME

BACKGROUND OF THE INVENTION

1. Field of the Invention

The present invention relates to a lambda-shaped carbazole and a main-chain NLO polyurethane containing the same.

2. Description of the Prior Art

Nonlinear Optical (NLO) materials can be categorized into two groups, i.e. organic and inorganic. Conventional inorganic NLO materials are $LiNbO_3$ or GaAs crystals. Organic NLO materials, as described in *Chemical Review* vol. 94, No.1, 31–76(1994) published by American Chemical Society, have higher electro-optical coefficients than inorganic NLO materials. It is also reported that organic NLO materials possess characteristics of high optical coefficiency, short response time, and ease of processing (G. R. Meredith, et al, *Macromolecules* 1982, 15, 1385). Although organic NLO materials possess the superior characteristics described above, they have the disadvantages of inferior thermal stability, low temporal stability of polarized dipole and relatively high optical loss.

In fabrication of organic NLO materials, organic NLO chromophore is incorporated into polymeric materials by blending. One example of these organic NLO materials is guest-host type NLO material. Organic NLO materials can also be fabricated by incorporating organic NLO chromophore into polymeric materials through chemical bonding reaction. Example of these organic NLO materials are main-chain, side-chain or cross-linking NLO polymers.

In a main-chain NLO polymer, the dipole of a chromophore can be parallel to the main chain of a polymer to form head-to-tail main-chain NLO polymers (G. A. Lindsay et al. *Macromolecules* 1992, 25, 6075, and C. Wu et al. *Macromolecules* 1992, 25, 6716), or the dipole of a chromophore can be perpendicular to the main chain of a polymer to form shoulder-to-shoulder main-chain NLO polymer( N. Tsutsumi et al., *Macromolecules* 1996, 29, 592) and I. Teraoka et al. *J. Appl. Phys.* 1991, 69, 2568).

In head-to-tail main-chain NLO materials, the high driving voltage can cause significantly low effective order parameters, especially when the molecular weight is high enough to cause chain-entanglement; and the molecular structure thereof is more difficult to be ordered by electric field. This limits head-to-tail main-chain NLO polymers' practical applications. In the shoulder-to-shoulder main-chain NLO materials, however, the aligning efficiency in electric field is raised because the dipole alignment of chromophores is perpendicular to the main chain of the polymer (*Theory of Polymer Dynamics Oxford University Press: Oxford* 1987", M. Doi and S. F. Edward). The solid stick-like structure increases the stability of the NLO coefficients of the materials at low temperatures. However, the solid stick-like structure also increases the local free volume between main chains of the material. The expanded local free volume may cause rapid relaxation when the temperature approaches the glass transition temperature of the material.

Accordingly, an ideal main-chain NLO material should possess both high poling efficiency in electric field and good thermal stability of NLO coefficients at high temperatures. However, in choosing polymeric materials for the main-chain NLO materials, some limitations should be considered, for example, polyacrylate and polymethacrylate have a glass transition temperature ($T_g$) of $-105°$ C., and thus are unstable under the actual application temperature. Polyimide, despite a high glass temperature when used in main-chain NLO materials, shows poor poling efficiency in electric field and low solubility. Accordingly, polyimide also has limited application in main-chain NLO materials. Polyurethane, however, thanks to ease of synthesis, good film-forming ability, and a glass transition temperature that can be modified by incorporating aromatic structure with different degrees of rigidity, has become an important base polymer of main-chain NLO materials ( S. S. H. Ma et al. (*Chem. Mater.* 1998, 10, 146).

In choosing NLO chromophores, two aspects should be considered. The first is whether the behavior of the chromophores per se, with respect to the NLO materials is stable after being incorporated into the polymers. For example, the size of the chromophores and the resonance length thereof will affect the alignment stability of dipole, the thermal stability of chromophores can be improved by increasing the resonance length, and the bulky structure can improve the volatility of the chromophores. Another aspect is the phase-matched phenomena of the NLO material. Generally, the phase-matched phenomena of the material can be improved by changing the structure of chromophores. However, conventionally, the phase match of second-order NLO coefficients is improved by adjusting the dielectric constant of materials. Recently, it has been found that the phase-matched phenomena can be improved by elevated off-diagonal components(i.e. $d_{31}$, $d_{32}$ . . . ). It has also been reported that carbazoles can be the base structures of the NLO chromophores because carbazoles possess a variety of electro-optical properties, such as photoconductivity ( B. Kippelen et al., *J. Phys. Rev. B* 1993, 48, 10710) and Y. Zhang et al., *Appl. Phys. Lett.* 1994, 66, 2561). It has also been disclosed that NLO chromophores with two-dimensional structure can be easily fabricated from carbazoles, because they possesses isoelectronic structure at 3rd and 6th positions (H. Yamamoto et al., *Appl. Phys. Lett.* 1992, 60, 935, X. T. Tao et al., *Chem. Mater.* 1995, 6, 1961, and X. T. Tao et al., *J. Polym. Sci. B. Polym. Phys.* 1995, 33, 2205). By using a two-dimensional carbazole, phase-matched second-harmonic coefficients can be significantly improved.

SUMMARY OF THE INVENTION

One object of the present invention is to provide a two-dimensional chromophore containing a lambda-shaped carbazole. The two-dimensional chromophore can increase the phase-matched second-harmonic coefficient.

Another object of the present invention is to provide a main-chain NLO polyurethane containing lambda-shaped chromophores.

The lambda-shaped carbazole has the following structure:

wherein,

R$^1$ and R$^2$ are the same or different, independently selected from the group consisting of (—CH$_2$—)$_n$ wherein n=2–11, (—CH$_2$CH$_2$O—)$_m$ wherein m=1–4, phenylene and naphthalene;

R$_3$ represents H(—CH$_2$—)$_n$ wherein n=2–11 or H(—CH$_2$CH$_2$O—)$_m$ wherein m=1–4.

Preferably, the n of (—CH$_2$—)$_n$ is selected from n=2–6 and the m of (—CH$_2$CH$_2$O—)$_m$ is selected from m=1–3.

Preferred lambda-shaped carbazoles include but are not limited to 9-hexyl-3,6-di(2-(6-hydroxyhexyl)sulfonylphenyl)-ethenyl)-9H-carbazole, 9-hexyl-3,6-di(2-(3-hydroxypropyl)sulfonylphenyl)-ethenyl)-9H-carbazole, 9-hexyl-3,6-di(2-(4-hydroxyphenyl)sulfonylphenyl)-ethenyl)-9H-carbazole, or 9-hexyl-3,6-di(2-(5-hydroxynaphthyl)sulfonylphenyl)-ethenyl)-9H-carbazole.

The above lambda-shaped carbazole chromophore can reduce the plasticization caused by chromophore to the main chain of a polymer material, and thus the temporal stability of the nonlinear optical coefficients is increased.

The following structure further illustrates the main-chain NLO polyurethanes containing the lambda-shaped carbazole of the invention.

Aromatic (Ar) diisocyanate moiety is derived from monomers selected from diisocyanate or the derivatives thereof.

Preferably, the n of (—CH$_2$—)$_n$ is selected from n=2–6 and the m of (—CH$_2$CH$_2$O—)$_m$ is selected from m=1–3. The diisocyanate derivatives include but are not limited to p-phenylene diisocyanate, 2,6-toluene diisocyanate, naphthalene-1,5-diisocyanate, methylene di(p-phenylene isocyanate), 2,2'-di(p-isocyanato phenylene)propane, 2,2'-di(p-isocyanato phenylene)hexafluoropropane, 3,3'-tolidene-4,4'diisocyanate, 3,3'-dimethoxy-4,4'-diisocyanato biphenyl, 2,2'-di(4-isocyanato phenoxy)biphenyl or isophorone diisocyanate.

Preferred main-chain NLO polyurethanes are the polymerization products of 9-hexyl-3,6-di(2-(3-hydroxypropyl)sulfonylphenyl)-ethenyl)-9H-carbazole and 2,2-di(p-isocyantophenylene)hexaflouropropane; 9-hexyl-3,6-di(2-(3-hydroxypropyl)sulfonylphenyl)-ethenyl)-9H-carbazole and 3,3'-dimethoxy-4,4'-diisocyanto biphenyl; or 9-hexyl-3,6-di(2-(3-hydroxypropyl)sulfonylphenyl)-ethenyl)-9H-carbazole and 2,2'-di(4-isocyanato phenoxy)biphenyl.

The main-chain NLO polyurethanes have a higher alignment stability in electric field because the dipole thereof is perpendicular to the main chain of the polymer, and thus the NLO coefficient is stabilized. The off-diagonal component $d_{33}$ of the NLO materials is between 28–36, the $d_{31}$ is between 8–12, and the $d_{33}/d_{31}$ ratio is about 3.

Hereinafter, the present invention will be described in more detail with reference to the Examples and drawings, however, it should be noted that the present invention is not limited to those Examples.

wherein,

R$^1$ and R$^2$ are the same or different, independently selected from the group consisting of (—CH$_2$—)$_n$ wherein n=2–11, (—CH$_2$CH$_2$O—)$_m$ wherein m=1–4, phenylene and naphthalene;

R$_3$ represents H(—CH$_2$—)$_n$ wherein n=2–11 or H(—CH$_2$CH$_2$O—)$_m$ wherein m=1–4.

DETAILED DESCRIPTION OF THE INVENTION

EXAMPLE 1

Synthesis of 9-Hexyl-9H-carbazole

20 g of carbazole was dissolved in 100 mL dry N,N-dimethyl acetamide (DMAc) in a 500 mL round bottomed flask. NaH (60% in mineral oil) was added into the flask slowly in nitrogen to form a mixture. The mixture was stirred for 20 minutes in ice/water bath. 30 g of 1-bromohexane was then added slowly to the flask and stirred for 6 hours in ice/water bath. The resulting solution was poured into 2L deionized water and extracted with ethyl acetate several times. The extract was re-extracted by deionized water. The final extract was concentrated by a rotary evaporator and further purified by column chromatography. A product of the following structure was obtained.

EXAMPLE 2

Synthesis of 9-Hexyl-9H-3,6-diformyl Carbazole

30 g dry N,N-dimethyl formamide(DMF) was dissolved in $POCl_3$ solution in a 500 mL round bottomed flask in ice/water bath. After the solution reached room temperature, 9-Hexyl-9H-carbazole dissolved in 50 mL 1,2-dichloroethane was charged into the solution slowly. The mixture was heated to 90° C. and reacted at the temperature for 24 hours. Then the hot mixture was poured into 500 mL 5% sodium hydroxide aqueous ice solution and extracted with dichloromethane several times. The organic fraction was extracted repeatedly with deionized water. The extract was dried over anhydrous magnesium sulfate and then concentrated by a rotary evaporator and further purified by column chromatography. A product of the following structure was obtained.

EXAMPLE 3

Synthesis of 4-Methylphenyl-6'-hydroxyhexyl Sulfide

5 g of p-methylthiolphenol, 6.7 g of potassium carbonate and 30 mL of dry DMF were added to a 250 mL 2-neck round bottomed flask and stirred for 30 minutes in nitrogen. Then 6.6 g of 6-chloro-1-hexanol was added into the mixture. The solution was heated to 70° C. and reacted for 12 hours. After reaction was complete, the solution was poured into 500 mL of deionized water and extracted by ethyl acetate several times. Then the organic fraction was extracted with deionized water three times. The extract was dried over anhydrous magnesium sulfate and concentrated by a rotary evaporator. The concentrate was further purified by column chromatography to produce a clear liquid. The yield was 98% and a product of the following structure was obtained.

EXAMPLE 4

Synthesis of 4-Methylphenyl-6'-acetoxyhexyl Sulfide

8.85 g of 4-Methylphenyl-6'-hydroxyhexyl sulfide, 8.06 g of acetic anhydride and 40 mL of acetic acid were added to a 250 mL round bottomed flask. The solution was heated to 70° C. and reacted for 6 hours. After reaction was complete, excess acetic anhydride and acetic acid was removed by distillation under reduced pressure. After that, the resulting crude product was dissolved in 300 mL of ethyl acetate and then washed by potassium carbonate solution and deionized water three times. The organic fraction was dried over anhydrous magnesium sulfate and then concentrated by a rotary evaporator. The concentrate was further purified by column chromatography to produce a clear liquid. The yield was 97% and a product of the following structure wasobtained.

EXAMPLE 5

Synthesis of 4-[(6-acetoxyhexyl)sulfonyl]toluene

10.2 g of 4-Methylphenyl-6'-acetoxyhexyl sulfide, and 20 mL of acetic acid were added to a 250 mL round bottomed flask. 10.8 g of 30% hydrogen peroxide was charged into the flask slowly. The solution was heated to 70° C. and reacted for 5 hours. After reaction was complete, excessive acetic acid was removed by distillation under reduced pressure. After that, the resulting crude product was dissolved in 300 mL of ethyl acetate and then washed by potassium carbonate solution and deionized water three times. The organic fraction was dried over anhydrous magnesium sulfate and then concentrated by a rotary evaporator. The concentrate was further purified by column chromatography to produce a clear sticky liquid having the following structure.

EXAMPLE 6

Synthesis of 4-[(6-acetoxyhexyl)sulfonyl]benzyl Bromide

2.0 g of 4-[(6-acetoxyhexyl)sulfonyl]toluene, 1.3 g of N-bromo-succinimide (NBS), 0.015 g of benzoyl peroxide (BPO) , and 20 mL of carbon tetrafluoride were added to a 250 mL round bottomed flask and heated with reflux for 12 hours in nitrogen. The mixture was allowed to cool down and then filtered. The filtrate was washed by deionized water repeatedly. The organic fraction was dried over anhydrous magnesium sulfate and then concentrated by a rotary evaporator. The concentrate was further purified by re-crystallization to produce a white solid. The yield was 71% with the following structure.

EXAMPLE 7

Synthesis of 4-[(6-acetoxyhexyl)sulfonyl]benzyl Diethyl Phosphate

2.9 g of 4-[(6-acetoxyhexyl)sulfonyl]benzyl bromide, and 15 mL of dried triethyl phosphorous ester(P(OEt)$_3$) were poured into a 250 mL round bottomed flask and heated with reflux for 6 hours in nitrogen. Excessive triethyl phosphorous ester was removed by distillation under reduced pressure. After that, the resulting crude product was dissolved in 100 mL of ethyl acetate and then washed by 100 mL of deionized water three times. The organic fraction was dried over anhydrous magnesium sulfate and then concentrated by a rotary evaporator. The concentrate was further purified by column chromatography to produce a clear sticky liquid. The yield was 83% with the following structure.

EXAMPLE 8

Synthesis of 9-Hexyl-3,6-di(2'-(6-hydroxyhexyl)sulfonylphenyl)-1'-ethenyl)-9H-carbazole(HSC)20 Monomer

0.32 g of sodium hydride(60% in mineral oil)and 5 mL of dried tetrahydrofuran(THF) were added to a 150 mL 2-neck round bottomed flask in ice bath and nitrogen to obtain a suspension solution. 0.5 g of 9-hyxyl-9H-3, 6-diformyl carbazole and 2.34 g of 4-[(6-acetoxyhexyl)sulfonyl]benzyl diethyl phosphate were dissolved in 5 mL of dried THF to obtain a mixed solution. The mixed solution was then added to the suspension solution in the 2-neck round flask dropwise, and reacted. 20 mL of deionized water was added to the reaction mixture to terminate the reaction after 4 hours. THF was removed by a rotary evaporator and then 50 mL methanol and 50 mL 25% Sulfuric acid solution were added thereto, and heated with reflux for 12 hours to undergo the hydrolysis reaction. The reaction solution was thereafter cooled down and neutralized with sodium carbonate, and methanol was removed by a rotary evaporator. Aqueous solution was removed by decantation, and the resulting crude product was dissolved in ethyl acetate and dried over anhydrous magnesium sulfate and then concentrated by a rotary evaporator. The resulting concentrate was further purified by column chromatography to produce a yellow sticky clear liquid having the following structure.

EXAMPLE 9

Synthesis of Main-chain Type NLO Polyurethanes Containing Lambda-shaped Carbazols PU-HSC (Polyurethanes)

1.02 g of 9-Hexyl-3,6-di(2'-(6-hydroxyhexyl)sulfonylphenyl)-1'-ethenyl)-9H-carbazole was dissolved in 5 mL of dried N-methylpyrrolidone (NMP) in nitrogen to obtain a solution. 0.3257 g of 4,4'-methylene bis(phenyl isocyanate (MDI monomers, Lancast, Britain) was added to the solution to obtain a mixture. The mixture was heated to 100° C. and reacted for 6 hours. The reaction mixture was then dropped into 100 mL of methanol to precipitate. The precipitate was filtrated and then dissolved in NMP. A crude product was obtained after re-precipitating with methanol three times. A yellow solid was finally obtained after filtration and drying. The final product has the following structure.

The structures and characteristics of the carbazole based chromophore obtained in example 8 and the main-chain type NLO Polyurethanes containing lambda-shaped carbazoles obtained in Example 9 were tested and identified by various instruments.

Figure 1:
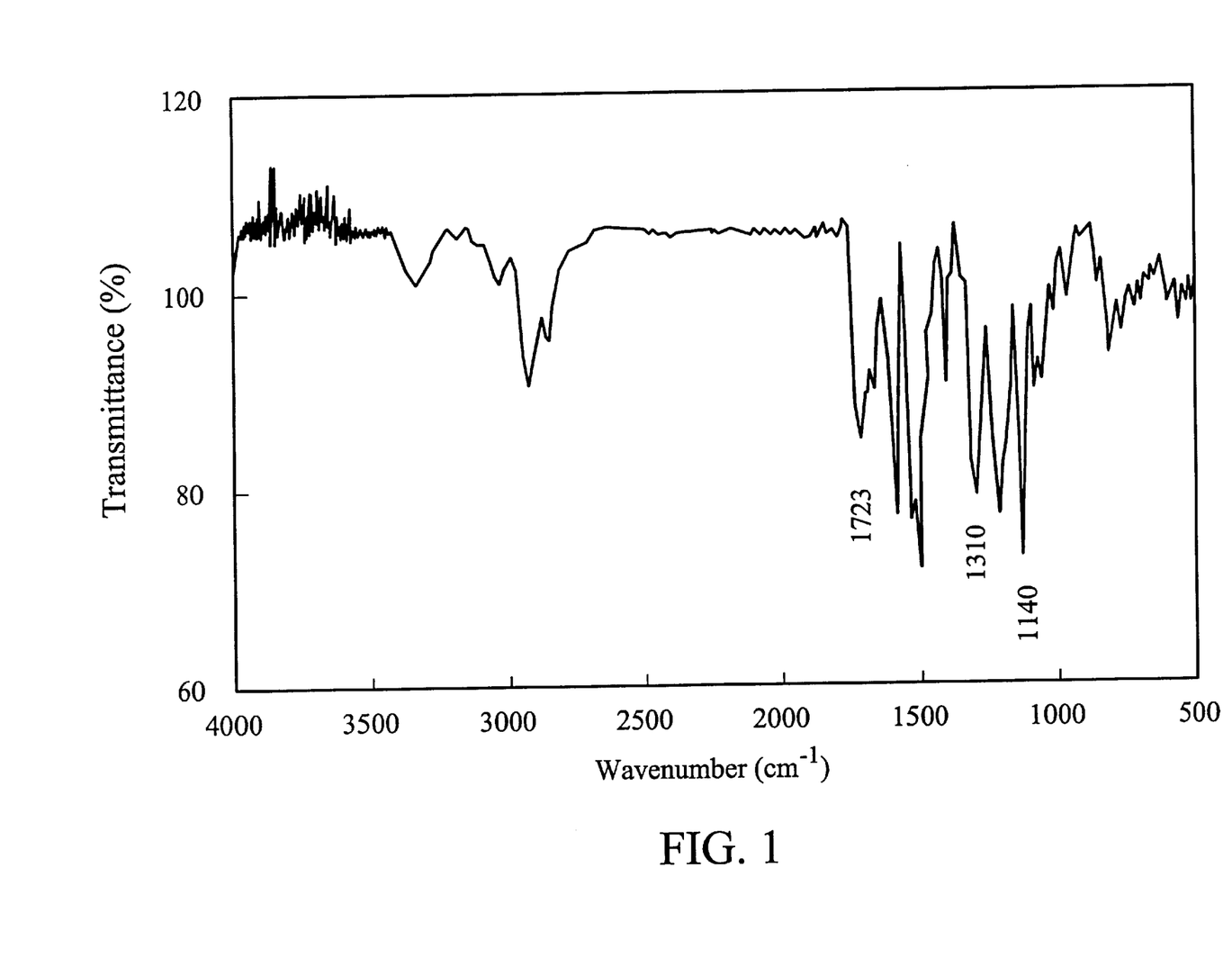
FIG. 1 is a graph showing the FT-IR spectra of the PU-HSU synthesized in Example 9 according to the present invention.

Fourier-transform infrared spectrometer (Bio-Rad, scanning wave number: 400 cm$^{-1}$ to 4000 cm$^{-1}$; KBr) and Nuclear magnetic resonance spectrometer, $^1$H-NMR (Bruker AM-400, operation frequency: 300 MHz; solvent: CDCl$_3$ or d$_6$-DMSO) were used to identify the structure of the main-chain NLO polyurethanes (PU-HSC). FIG. 1 shows the FT-IR spectra of the PU-HSU synthesized in Example 9. As can be seen, an absorption at 1723 cm$^{-1}$ appears, while no absorption of isocyanate from diisocyanate monomers is shown at nearby 2300 cm$^{-1}$. $^1$H-NMR of the NLO polyurethanes indicates that chemical shift of urethanes proton is on 9.45 ppm, chemical shift of aliphatic proton near sulfonyl group is on 3.28 ppm, and chemical shift of methylene proton near isocyanate is on 2.68 ppm.

Moreover, the NMR data and element analysis data of compounds synthesized in Example 1 to Example 9 are respectively summarized in table 1 and table 2 below.

TABLE 1

|   | compound | $^1$H-NMR (CDC13) δ: ppm |
|---|---|---|
| example 1 | 9-Hexyl-9H-carbazole | 0.83–0.87 (t, 3H, —C$\underline{H}_3$), 1.25–1.40 (m, 6H, —C$\underline{H}_2$—), 1.82–1.88 (p, 2H, —N—CH$_2$—C$\underline{H}_2$—), 4.26–4.30 (t, 2H, —N—C$\underline{H}_2$—), 7.20–7.24 (t, 2H, Ar—$\underline{H}$, para to NH), 7.38–7.41 (d, 2H, Ar—$\underline{H}$, ortho to NH), 7.43–7.47 (t, 2H, Ar—$\underline{H}$, meta to NH), 8.08—8.10 (d, 2H, AR—H, ortho to NH) |
| example 2 | 9-Hexyl-9H-3,6-diformyl carbazole | 0.76—0.80 (t, 3H, —C$\underline{H}_3$), 1.17–1.32 (m, 6H, —C$\underline{H}_3$—), 1.80–(p, 2H, —N—CH$_2$—C$\underline{H}_2$—), 4.27–4.30 (t, 2H, C$\underline{H}_2$—), 7.44–7.46 (d, 2H, Ar—$\underline{H}$, ortho to NH), 7.98–8.00 (d, 2H, Ar—$\underline{H}$, ortho to CHO), 8.55 (s, 2H, Ar—$\underline{H}$, ortho to CHO), 10.04 (s, 2H, C$\underline{H}$O) |
| example 3 | 4-Methylphenyl-6'-hydroxyhexyl sulfide | 1.31–1.63 (m, 8H, —C$\underline{H}_2$—), 2.29 (s, 3H, Ph—C$\underline{H}_3$), 2.85 (t, 2H, S—C$\underline{H}_2$), 3.60 (t, 3H, O—C$\underline{H}_2$—), 7.06 (d, 2H, Ar—H, ortho to SC$\underline{H}_2$—), 7.23 (d, 2H, Ar—H, ortho to CH$_3$) |
| example 4 | 4-Methylphenyl-6'-acetoxyhexyl sulfide | 1.28–1.61 (m, 8H, —C$\underline{H}_2$—), 1.99 (s, 3H, —O—C(O)—C$\underline{H}_3$), 2.27 (s, 3H, Ph—C$\underline{H}_3$), 2.82 (t, 2H, S—C$\underline{H}_2$), 4.00 (t, 3H, —COO—C$\underline{H}_2$—), 7.03 (d, 2H, Ar—H, ortho to S—C$\underline{H}_2$—), 7.20 (d, 2H, Ar—H, ortho to CH$_3$) |
| example 5 | 4-[(6-acetoxyhexyl)sulfonyl] toluene | 1.23–1.64 (m, 8H, —C$\underline{H}_2$—), 1.94 (s, 3H, —O—C(O)—C$\underline{H}_3$), 2.37 (s, 3H, Ph—C$\underline{H}_3$), 2.98 (t, 2H, SO$_2$—C$\underline{H}_2$—), 3.93 (t, 3H, —COO—C$\underline{H}_2$—), 7.28 (d, 2H, Ar—H, ortho to SO$_2$—), 7.69 (d, 2H, Ar—H, ortho to CH$_3$) |
| example 6 | 4-[(6-acetoxyhexyl)sulfonyl] benzyl bromide | 1.31–1.71 (m, 8H, —C$\underline{H}_2$—), 2.00 (s, 3H, —O—C(O)—C$\underline{H}_3$), 3.05 (t, 2H, SO$_2$—C$\underline{H}_2$—), 3.98 (t, 3H, —COO—CH$_2$—), 4.48 (s, 3H, Ph—C$\underline{H}_2$Br),7.55 (d, 2H, Ar—H, ortho to SO$_2$—), 7.85 (d, 2H, Ar—H, ortho to CH$_3$) |
| example 7 | 4-[(6-acetoxyhexyl)sulfonyl] benzyl diethyl phosphate | 1.20 (t, 6H, P—OCH$_2$—C$\underline{H}_3$), 1.23–1.70 (m, 8H, —CH$_2$—), 1.98 (s, 3H, —O—C(O)—C$\underline{H}_3$), 3.01 (t, 2H,SO$_2$—C$\underline{H}_2$—), 3.15 (d, 2H,Ph—C$\underline{H}_2$—P(O) (OEt)$_2$, J = 22.16 Hz), 3.98 (t, 3H, —COO—C$\underline{H}_2$—). 7.55 (d, 2H, Ar—H, ortho to CH$_2$P(O) (OEt)$_2$), 7.85 (d, 2H, Ar—H, ortho to SO$_2$—) |
| example 8 | 9-Hexyl-3,6-di(2-(6-hydroxyhexyl)sulfonyl phenyl)-ethenyl)-9H-carbazole | 1.20–1.81 (m, 22H, —CH$_2$—), 2.36 (s, 2H, —O$\underline{H}$), 3.04 (t, 4H, SO$_2$—C$\underline{H}_2$—), 3.52 (t, 4H, —CH$_2$—OH), 4.18 (t, 2H, —N—C$\underline{H}_2$—), 7.07 (d, 2H, CH=C$\underline{H}$—PhSO$_2$—, J = 16.24 Hz), 7.24 (d, 6H, Ar—H, meta to SO$_2$— and ortho to vinyl group), 7.30 (d, 2H, C$\underline{H}$=CH—PhSO$_2$—, J = 25.72 Hz), 7.68 (d, 6H, Ar—H, meta to SO$_2$— and ortho to vinyl group), 7.80 (d, 4H, Ar—H, ortho to SO$_2$—), 8.21 (s, 2H, Ar—H, ortho to vinyl group) |
| example 9 | Polyurethanes | 0.77 (3H, (—CH$_2$)$_5$C$\underline{H}_3$), 1.03–1.24 (16H, —C$\underline{H}_2$), 1.30, 1.52, 2.68 (2H, —Ph—C$\underline{H}_2$—Ph—), 3.27 (4H, SO$_2$—C$\underline{H}_2$—), 3.74 (4H, —C$\underline{H}_2$—O—), 3.97 (2H, —N—C$\underline{H}_2$—C$_5$H$_{11}$), 7.05 (—C=CH—P$\underline{H}$SO$_2$—), 7.29 (2H, C$\underline{H}$=CH—PhSO$_2$— and Ar—H, meta to urethane linkage), 7.33–7.50, 7.74–7.85 (4H, Ar—H, ortho to SO$_2$— and Ar—H, ortho to urethane linkage), 8.48 (2H, Ar—H, ortho to vinyl group), 9.44 (2H, —OCON$\underline{H}$—) |

TABLE 2

|   | compound | formula | Experiment Data | Analysis Data |
|---|---|---|---|---|
| example 1 | 9-Hexyl-9H-carbazole | C$_{18}$H$_{21}$N | C: 86.12% H: 8.31% N: 5.54% | C: 86.01% H: 8.42% N: 5.57% |
| example 2 | 9-Hexyl-9H-3,6-diformyl carbazole | C$_{20}$H$_{21}$NO$_2$ | C: 78.08% H: 6.83% N: 4.51% | C: 78.15% H: 6.89% N: 4.56% |
| example 3 | 4-Methylphenyl-6'-hydroxyhexyl sulfide | C$_{13}$H$_{20}$OS | C: 69.62% H: 8.87% | C: 69.59% H: 8.98% |
| example 4 | 4-Methylphenyl-6'-acetoxyhexyl sulfide | C$_{15}$H$_{22}$O$_2$S | C: 67.59% H: 8.34% | C: 67.63% H: 8.32% |
| example 5 | 4-[(6-acetoxyhexyl) sulfonyl] toluene | C$_{15}$H$_{22}$O$_4$S | C: 60.42% H: 7.41% | C: 60.38% H: 7.43% |
| example 6 | 4-[(6-acetoxyhexyl) sulfonyl] benzyl bromide | CD$_{15}$H$_{21}$O$_4$SBr | C: 47.69% H: 5.57% | C: 47.75% H: 5.61% |
| example 7 | 4-[(6-acetoxyhexyl) sulfonyl] benzyl diethyl phosphate | C$_{19}$H$_{31}$O$_7$PS | C: 52.47% H: 7.26% | C: 52.52% H: 7.19% |

TABLE 2-continued

| | compound | formula | Experiment Data | Analysis Data |
|---|---|---|---|---|
| example 8 | 9-Hexyl-3,6-di (2'-(6-hydroxyhexyl) sulfonyl phenyl)-1'-ethenyl)-9H-carbazole | $C_{24}H_{57}NO_6S_2$ | C: 69.43%<br>H: 7.53%<br>N: 1.84% | C: 70.46%<br>H: 7.33%<br>N: 1.79% |
| example 9 | Polyurethanes | $C_{61}H_{67}N_3O_8S_2$<br>(repeat unit) | C: 69.41%<br>H: 6.93%<br>N: 4.31% | C: 70.83%<br>H: 6.53%<br>N: 4.06% |

Figure 2:
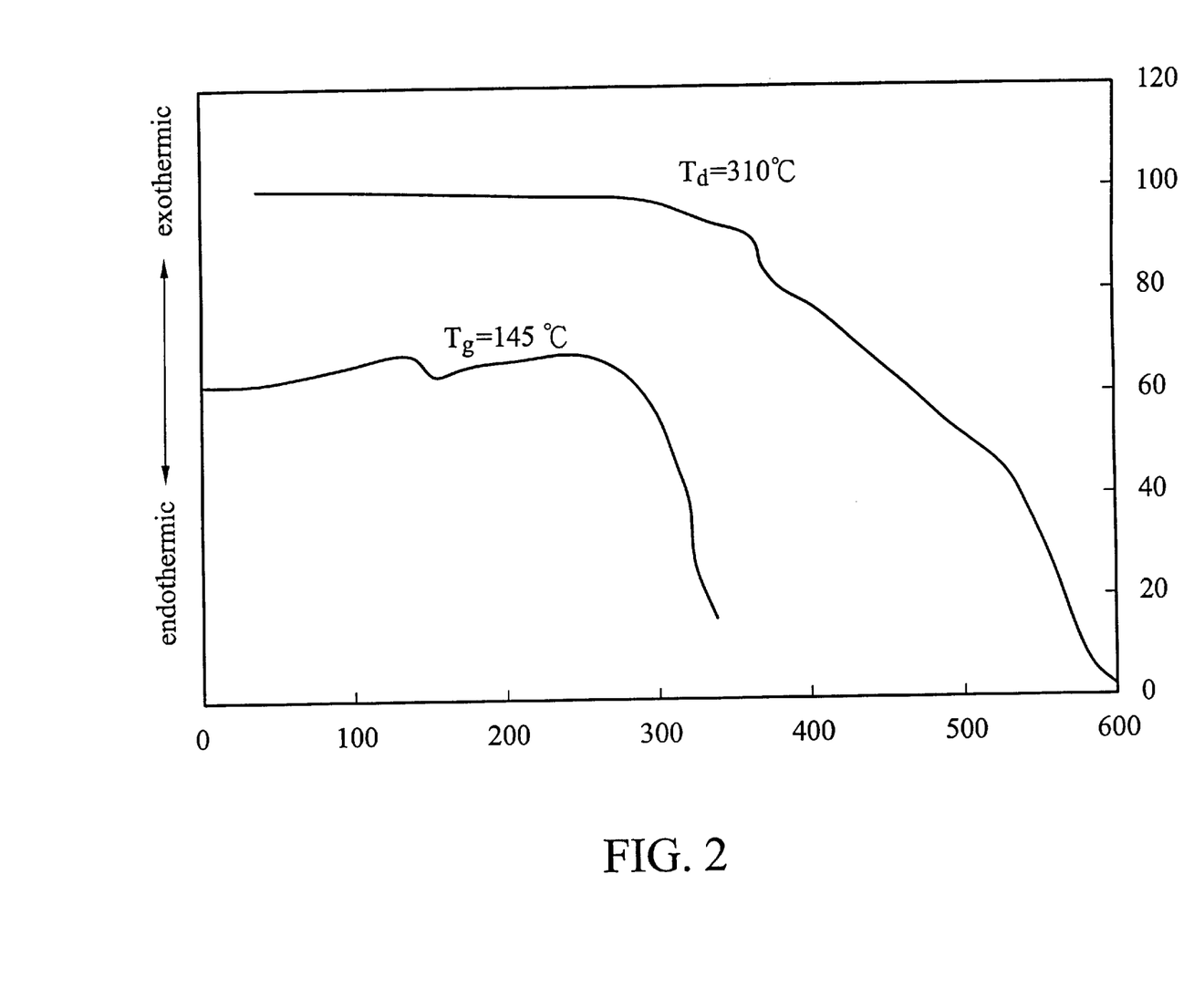
FIG. 2 is a graph showing the thermal analysis of the PU-HSU synthesized in Example 9 according to the present invention.

The glass transition temperature($T_g$) and the degradation temperature($T_d$) of the PU-HSU synthesized in Example 9 were measured using Differential scanning calorimeter (DSC, Seiko SSC/5200) and thermogravimetric analyzer (TGA, Seiko 2200). The DSC and TGA were operated at a heating rate of 10° C./min in 50 mL/min nitrogen atmosphere. The results are shown in FIG. 2, which indicates the glass transition temperature($T_g$) is about 145° C., and the degradation temperature($T_d$) of 5% weight loss is about 310° C.

The optoelectronic characteristics of the PU__HSC synthesized from Example 9 were also tested. The NLO polyurethane was first dissolved in an aprotic solvent, such as N,N-dimethyl formamide (DMF) N,N-dimethyl acetamide (DMAc) dimethylsulfoxide (DMSO) and N-methylpyrrolidone (NMP) at room temperature to form a solution. The solution was then coated on ITO glasses by spin coating technique to obtain transparent film specimens. The thickness of these transparent film specimens was controlled at a range of 1 to 2 micrometers.

The transparent film specimens were then subject to a corona poling process by using in-situ poling. The corona discharge was generated by using a tungsten filament probe disposed 1 cm above the transparent film specimens. The electric current flowing through these film specimens were between 0.2 to 1.0 A, and 1.064 m Nd:YaG laser was used to determine the $d_{33}$ and $d_{31}$ of the film specimens. The values of $d_{33}$ and $d_{31}$ are 34 pm/V and 11 pm/V, respectively.

The stability of the NLO coefficient of the film specimens with respect to temperature and time was also measured. The NLO coefficients (including $d_{33}$ and $d_{31}$) of the film specimens were measured by using a Q-switched Nd:YAG laser (wave length 1.064 m), and a Y-cut quartz crystal ($d_{11}$=0.5 pm/V)was used as reference. The stability of the film specimens after poling with respect to the change of time in different temperature was respectively shown in FIG. 3 and FIG. 4.

Figure 3:
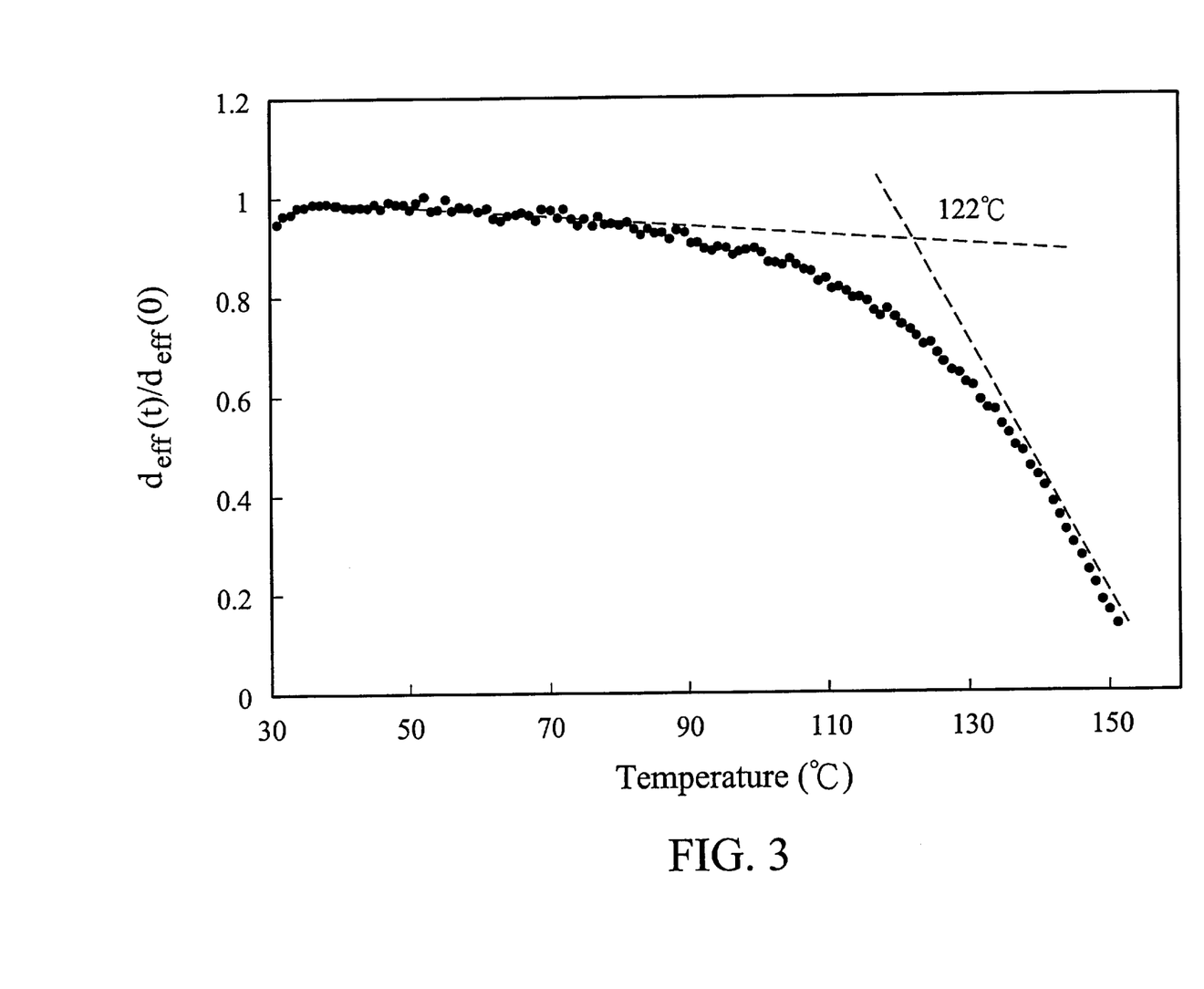
FIG. 3 is a graph showing the dynamic thermal stability of the PU-HSU synthesized in Example 9 according to the present invention.

As shown in FIG. 3, the NLO coefficient ($d_{eff}(t)/d_{eff}(0)$) is stable at 122° C., however, when the temperature is higher than 122° C., the value of the NLO coefficient decreases rapidly because the movement of the main-chain polymers induce rapid relaxation of the dipole alignment.

Figure 4:
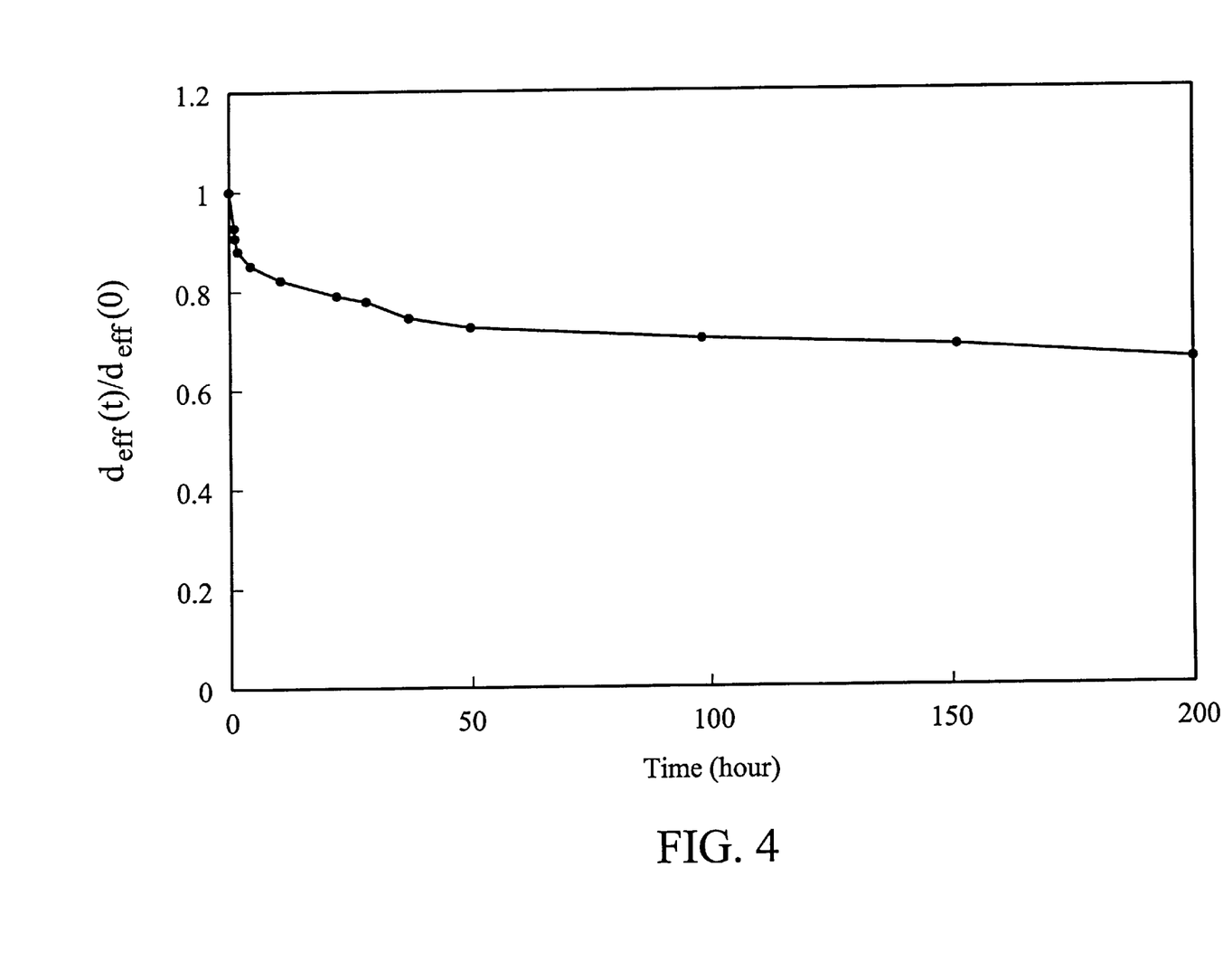
FIG. 4 is a graph showing the temporal stability under 100° C. of the PU-HSU synthesized in Example 9 according to the present invention.

As can be seen from FIG. 4, the value of the NLO coefficient decreases 20% rapidly at the beginning, however maintains at 62% of the value of the NLO coefficient even after 200 hours. This indicates that even operation temperature closes to the glass transition temperature of the material, the NLO coefficients thereof still show superior temporal stability, and thus incorporating chromophores into main-chain polymers can suppress the movement of the dipole effectively even when the temperature closes to the glass transition temperature of the material.

From the above results, it is known that the NLO polyurethanes obtained according the present invention possess excellent temporal stability at 100° C. Based on the structure design of the present invention, superior temporal stability is obtainable and the decline of NLO coefficients can be improved. The structure design also raises the actual application temperature to be close to the glass transition temperature of the material.

While the invention has been shown and described of the preferred embodiment thereof, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A main-chain type NLO polyurethane containing a lambda-shaped carbazole, and represented by the following formula:

wherein,
R$^1$ and R$^2$ are the same or different, independently selected from the group consisting of (—CH$_2$—)$_n$, wherein n=2–11, (—CH$_2$CH$_2$O—)$_m$, wherein m=1–4, phenylene and naphthalene; and
R$_3$ represents H(—CH$_2$—)$_n$, wherein n=2–11 or H(—CH$_2$CH$_2$O—)$_m$, wherein m=1–4.

2. The main-chain NLO polyurethanes according to claim 1, wherein the n of (—CH$_2$—)$_n$ group is selected from 2–6.

3. The main-chain NLO polyurethanes according to claim 1, wherein the m of (—CH$_2$CH$_2$O—)$_m$ group is selected from 1–3.

4. The main-chain NLO polyurethanes according to claim 1, wherein the aromatic (Ar) diisocyanate moiety is derived from monomers selected from the group consisting of p-phenylene diisocyanate, 2,6-toluene diisocyanate, naphthalene-1,5-diisocyanate, methylene di(p-phenylene isocyanate), 2,2-di(p-isocyanato phenylene)propane, 2,2-di(p-isocyanato phenylene)hexafluoropropane, 3,3'-tolidene-4,4'diisocyanate, 3,3'-dimethoxy-4,4'-diisocyanato biphenyl, 2,2'-di(4-isocyanato phenoxy)biphenyl and isophorone diisocyanate.

5. The main-chain NLO polyurethane according to claim 1, which is a polymerization product of 9-hexyl-3,6-di(2-(3-hydroxypropyl)sulfonylphenyl)-ethenyl)-9H-carbazole and 2,2-di(p-isocyantophenylene)hexaflouropropane.

6. The main-chain NLO polyurethane according to claim 1, which is a polymerization product of 9-hexyl-3,6-di(2-(3-hydroxypropyl)sulfonylphenyl)-ethenyl)-9H-carbazole and 3,3'-dimethoxy-4,4'-diisocyanto biphenyl.

7. The main-chain NLO polyurethane according to claim 1, which is a polymerization product of 9-hexyl-3,6-di(2-(3-hydroxypropyl)sulfonylphenyl)-ethenyl)-9H-carbazole and 2,2'-di(4-isocyanato phenoxy)biphenyl.

* * * * *